United States Patent [19]

Onoda et al.

[11] 4,335,258

[45] Jun. 15, 1982

[54] PROCESS FOR PRODUCING METHACRYLIC ACID

[75] Inventors: Takeru Onoda; Masayuki Otake, both of Yokohama; Jutaro Yamaguchi, Yamato, all of Japan

[73] Assignee: Mitsubishi Chemical Industries, Ltd. Angeles, Calif.

[21] Appl. No.: 109,219

[22] Filed: Jan. 3, 1980

[30] Foreign Application Priority Data

Jan. 16, 1979 [JP] Japan .................................. 54-3488

[51] Int. Cl.³ ..................... C07C 51/377; C07C 57/05
[52] U.S. Cl. .................................................. 562/599
[58] Field of Search ..................... 562/599; 560/214

[56] References Cited

U.S. PATENT DOCUMENTS 4,061,673  12/1977  Anoda et al. ...................... 562/599

FOREIGN PATENT DOCUMENTS 52-39622  3/1977  Japan ............................... 562/599

*Primary Examiner*—Vivian Garner
*Attorney, Agent, or Firm*—Oblon, Fisher, Spivak, McClelland and Maier

[57] ABSTRACT

Methacrylic acid is produced by oxidative dehydrogenation of isobutyric acid in vapor phase in the presence of a lithium salt of a heteropolyacid or a reduced form of the heteropolyacid.

3 Claims, No Drawings

PROCESS FOR PRODUCING METHACRYLIC ACID

BACKGROUND OF THE INVENTION

1. Field of the Invention

This invention relates to a process for producing methacrylic acid by oxidative dehydrogenation of isobutyric acid.

2. Description of the Prior Art

It is known that catalysts which contain a molybdophosphoric acid in which molybdenum may be partly replaced by vanadium and/or tungsten, and/or a reduced form thereof as a main component are used in the manufacture of methacrylic acid by oxidative dehydrogenation of isobutyric acid (Japanese Patent Laid-Open Application No. 78120/1973). Although the catalysts are highly active and suitable for use as catalyst for the production of methacrylic acid, they are not completely satisfactory with respect to catalyst life.

SUMMARY OF THE INVENTION

It has now been found that the lithium salts of the abovementioned heteropolyacids are highly active and have long life.

This invention provides a process for producing methacrylic acid by oxidative dehydrogenation of isobutyric acid in vapor phase in the presence of a catalyst, a lithium salt of a heteropolyacid having the general formula (I):

$$H_{3+x}Mo_{12-x-y}W_yV_xPO_{40} \quad (I)$$

wherein
x is 0, 1, 2 or 3;
y is 0, 1, 2 or 3; and
$0 \leq x+y \leq 4$;
or a reduced form of the heteropolyacid having the general formula (II):

$$H_{3+x+n}Mo_{12-x-y}W_yV_xPO_{40} \quad (II)$$

wherein
x and y are as defined herein above and
n is an integer of 1 to 8.

DETAILED DESCRIPTION OF THE PREFERRED EMBODIMENTS

The catalysts used in the process of this invention are lithium salts of a heteropolyacid having the general formula (I):

$$H_{3+x}Mo_{12-x-y}W_yV_xPO_{40} \quad (I)$$

wherein
x is 0, 1, 2 or 3;
y is 0, 1, 2 or 3; and
$0 \leq x+y \leq 4$;
or a reduced form of the heteropolyacid having the general formula (II):

$$H_{3+x+n}Mo_{12-x-y}W_yV_xPO_{40} \quad (II)$$

wherein
x and y are as defined herein above and
n is an integer of 1 to 8.

As lithium salts, acidic lithium salts are preferred. Especially, the lithium salts in which 0.05-3 gram-atoms, more preferably, 0.1-1 gram-atom of hydrogen per mole of the heteropolyacid is replaced by lithium show excellent catalytic efficiency.

Such lithium salts of the heteropolyacid can be readily obtained, for example, by adding a predetermined amount of a hydroxide, carbonate, nitrate, chloride or a salt of an organic acid such as acetate, oxalate or the like of lithium to an aqueous solution of the heteropolyacid. They can also be obtained by mixing the solid heteropolyacid and the solid lithium compound mentioned above and then shaping and calcining the mixture.

In the process of this invention, the catalyst component is usually supported on a carrier such as silica, alumina, silica-alumina, diatomaceous earth, carborundum, pumice, zeolite or the like for use. As the method of supporting the catalyst, any means such as impregnation, evaporation to dryness, neading followed by shaping or the like can be applied.

Incidentally, Japanese Pat. No. 41128/1978 discloses catalysts for producing methacrylic acid by oxidative dehydrogenation of isobutyric acid, which consist of molybdophosphoric acid or molybdovanadophosphoric acid to which an alkali metal sulfate is added.

However, in the case of the catalyst to which an alkali metal sulfate is added, the alkali metal is present not as a salt of heteropolyacid, but as a sulfate. That is to say, for example, the X-ray diffraction peaks of the crystals separated out of the aqueous solution which is obtained by adding lithium sulfate to an aqueous solution of 10-molybdo-2-vanadophosphoric acid clearly indicate the characteristics of free 10-molybdo-2-vanadophosphoric acid. In contrast to this, when lithium carbonate is used, the X-ray diffraction peaks of the obtained crystals indicate the characteristics of lithium salt of 10-molybdo-2-vanadophosphoric acid, which can be clearly distinguished from the former.

The oxidative dehydrogenation of isobutyric acid in vapor phase according to this invention is usually effected by contacting a gas mixture of isobutyric acid having a concentration of 0.5 to 10 mol % and oxygen having a molar ratio to isobutyric acid of 0.1 to 10, preferably 0.5 to 5.0, with the above-mentioned catalyst at a temperature of 200° to 500° C. under a pressure of 0.5 to 30 kg/cm²G for a period of about 0.01 to 20 seconds. The raw material gas mixture is preferably diluted with a gas which is inert to the reaction, such as nitrogen, water vapor, carbon dioxide or the like. Alternatively, the off-gas of the oxidative dehydrogenation can also be used as diluent as it is or after being oxidized. Commercially attractive conversions of isobutyric acid and selectivities to methacrylic acid can be achieved by the process of this invention using the catalyst having high activity and long life.

Having generally described this invention, a more complete understanding can be obtained by reference to certain examples and comparative examples which are provided herein for purposes of illustration only and are not intended to be limiting in any manner.

EXAMPLE 1

To a 75 wt.% aqueous solution of 10-molybdo-2-vanadophosphoric acid (H₅Mo₁₀V₂PO₄₀.32H₂O) was added in portions powdery lithium carbonate with stirring. The lithium carbonate was added in an amount of 0.05, 0.25 and 0.5 mole per mole of 10-molybdo-2-vanadophosphoric acid to prepare three kinds of aqueous solutions of lithium salt of 10-molybdo-2-vanadophosphoric acid.

In the above-mentioned three kinds of aqueous solutions were immersed commercially available spherical shaped diatomaceous earth carrier (4 mm$\phi$) overnight. The carrier was lifted up from the vessel and dried at 130° C. to prepare three kinds of catalysts having a content of the catalyst component of 45 wt.%.

Into a stainless steel (SUS-316) tubular reactor having an inner diameter of 1 inch was charged 3 ml of the prepared catalyst described above. Then, a gas having the following composition:

| isobutyric acid | 5 mole % |
|---|---|
| water vapor | 10 mole % |
| oxygen | 5 mole % |
| nitrogen | 80 mole % | was passed at a temperature of 320° C. and at a space velocity (GHSV) of 15,000 hr$^{-1}$ to carry out the oxidative dehydrogenation of isobutyric acid.

In the following Table 1, the composition of the catalysts used and the corresponding results of the early stage of the reaction (the conversion of isobutyric acid and the selectivity to methacrylic acid) are shown.

TABLE 1

| Catalyst No. | Composition of the heteropolyacid salt | Conversion of isobutyric acid (%) | Selectivity to methacrylic acid (%) |
|---|---|---|---|
| 1 | $H_{4.9}Li_{0.1}Mo_{10}V_2PO_{40}$ | 31 | 69 |
| 2 | $H_{4.5}Li_{0.5}Mo_{10}V_2PO_{40}$ | 39 | 69 |
| 3 | $H_4Li_1Mo_{10}V_2PO_{40}$ | 29 | 68 |

EXAMPLE 2

In the same manner as in Example 1 with the exception that 0.5 mole of lithium chloride per mole of 10-molybdo-2-vanadophosphoric acid was used in place of lithium carbonate, a catalyst in which lithium salt of 10-molybdo-2-vanadophosphoric acid ($H_{4.5}Li_{0.5}Mo_{10}V_2PO_{40}$) was supported on the spherical shaped diatomaceous earth carrier was prepared.

Using this catalyst, the oxidative dehydrogenation of isobutyric acid was carried out under the same reaction conditions as in Example 1. As the result, the conversion of isobutyric acid was 34%, and the selectivity to methacrylic acid was 70%.

COMPARATIVE EXAMPLE 1

Catalyst preparation was carried out in the same manner as in Example 1 with the exception that lithium carbonate was not employed, obtaining a catalyst with a content of 10-molybdo-2-vanadophosphoric acid of 45 wt.%.

Using this catalyst, the oxidative dehydrogenation of isobutyric acid was carried out under the same reaction conditions as in Example 1. As the result, the conversion of isobutyric acid was 29.3%, and the selectivity to methacrylic acid was 69%.

COMPARATIVE EXAMPLE 2

A catalyst was prepared in the same manner as in Example 1, with the exception that 0.25 mole of lithium sulfate ($Li_2SO_4 \cdot H_2O$) per mole of 10-molybdo-2-vanadophosphoric acid was used in place of lithium carbonate.

Using this catalyst, the oxidative dehydrogenation of isobutyric acid was carried out under the same reaction conditions as in Example 1. As the result, the conversion of isobutyric acid was 31.6%, and the selectivity to methacrylic acid was 66%.

COMPARATIVE EXAMPLE 3

In the same manner as in Example 1 with the exception that 0.5 mole of sodium carbonate per mole of 10-molybdo-2-vanadophosphoric acid was used in place of lithium carbonate, a catalyst supporting sodium salt of 10-molybdo-2-vanadophosphoric acid was prepared. Using this catalyst, the oxidative dehydrogenation of isobutyric acid was carried out under the same reaction conditions as in Example 1. As the result, the conversion of isobutyric acid was 15%, and the selectivity to methacrylic acid was 59%.

EXAMPLE 3 AND COMPARATIVE EXAMPLE 4

Using Catalyst-3 prepared in Example 1 and the catalyst prepared in Comparative Example 1, the oxidative dehydrogenation of isobutyric acid was carried out under the same conditions as in Example 1 except that the reaction temperature was changed to 325° C., and the variation of catalytic activity with time was investigated. The results are shown in Table 2 below.

TABLE 2

| | Reaction Time (hr.) | 100 | 200 | 400 | 650 |
|---|---|---|---|---|---|
| Example 3 | Conversion of isobutyric acid (%) | 29.8 | 28.4 | 28.0 | 28.5 |
| | Selectivity to methacrylic acid (%) | 69.5 | 70.0 | 69.5 | 69.5 |
| Comparative Example 4 | Conversion of isobutyric acid (%) | 32.7 | 28.8 | 23.8 | 21.2 |
| | Selectivity to methacrylic acid (%) | 67.5 | 66.6 | 65.0 | 64.6 |

Having now fully described the invention, it will be apparent to one of ordinary skill in the art that many changes and modifications can be made thereto without departing from the spirit of the invention as set forth herein.

What is claimed as new and intended to be covered by Letters Patent is:

1. A process for producing methacrylic acid which comprises oxidatively dehydrogenating isobutyric acid in vapor phase in the presence of a lithium salt of a heteropolyacid having the general formula:

$$H_{3+x-z}Li_zMo_{12-x-y}W_yV_xPO_{40}$$

wherein
X is 0, 1, 2 or 3;
y is 0, 1, 2 or 3;
$0 \leq x+y \leq 4$; and
$0.05 \leq z \leq 3$;
or a reduced form of the heteropolyacid having the general formula:

$$H_{3+x-z+n}Li_zMo_{12-x-y}W_yV_xPO_{40}$$

wherein x, y and z are as defined herein above and n is an integer of 1 to 8.

2. The process according to claim 1 wherein the oxidative dehydrogenation is conducted in the presence of the lithium salt of heteropolyacid having the general formula:

$$H_{3+x-z}Li_zMo_{12-x}V_xPO_{40}$$

wherein
x is 0, 1, 2, or 3; and
$0.05 \leqq z \leqq 3$;
or the reduced form thereof having the general formula:

$$H_{3+x-z+n}Li_zMo_{12-x}V_xPO_{40}$$

wherein x and z are as defined herein above and n is an integer of 1 to 8.

3. The process according to claim 2 wherein the oxidative dehydrogenation is conducted in the presence of the lithium salt of heteropolyacid having the general formula:

$$H_{5-z}Li_zMo_{10}V_2PO_{40}$$

wherein $0.1 \leqq z \leqq 1$; or the reduced form thereof having the general formula:

$$H_{5-z+n}Li_zMo_{10}V_2PO_{40}$$

wherein z is as defined herein above and n is an integer of 1 to 8.

* * * * *